United States Patent
Adamson et al.

(10) Patent No.: US 11,129,522 B2
(45) Date of Patent: Sep. 28, 2021

(54) METHOD AND MEASUREMENT SYSTEM FOR OPTICALLY MEASURING AN OBJECT

(71) Applicant: DENTSPLY SIRONA Inc., York, PA (US)

(72) Inventors: Anders Adamson, Darmstadt (DE); Frank Thiel, Ober-Ramstadt (DE); Ulf Willers, Seeheim-Jugenheim (DE)

(73) Assignee: DENTSPLY SIRONA INC., York, PA (US)

( * ) Notice: Subject to any disclaimer, the term of this patent is extended or adjusted under 35 U.S.C. 154(b) by 31 days.

(21) Appl. No.: 16/508,871

(22) Filed: Jul. 11, 2019

(65) Prior Publication Data

US 2019/0328222 A1    Oct. 31, 2019

Related U.S. Application Data

(63) Continuation of application No. 15/564,436, filed as application No. PCT/EP2016/057870 on Apr. 11, 2016, now Pat. No. 10,390,693.

(30) Foreign Application Priority Data

Apr. 9, 2015 (DE) .......................... 102015206341.0

(51) Int. Cl.
*A61B 1/24* (2006.01)
*A61B 5/00* (2006.01)
*A61C 9/00* (2006.01)
*G01B 11/24* (2006.01)
*G01B 9/02* (2006.01)
*G01B 11/02* (2006.01)

(52) U.S. Cl.
CPC .............. *A61B 1/24* (2013.01); *A61B 5/0088* (2013.01); *A61C 9/006* (2013.01); *A61C 9/0066* (2013.01); *G01B 9/0203* (2013.01); *G01B 11/022* (2013.01); *G01B 11/24* (2013.01); *G01B 2210/52* (2013.01)

(58) Field of Classification Search
CPC ....... A61B 1/24; A61B 5/0088; G01B 11/022; G01B 9/0203; G01B 11/24; G01B 2210/52; A61C 9/006; A61C 9/0066
See application file for complete search history.

(56) References Cited

U.S. PATENT DOCUMENTS 4,129,359 A * 12/1978 Momiyama .............. G02B 9/34
                                                                  359/675
5,115,307 A *  5/1992 Cooper .............. A61B 1/00091
                                                                  348/66

(Continued)

FOREIGN PATENT DOCUMENTS

CN       1164033 A       5/2007
DE       10043749 A1     3/2002

(Continued)

*Primary Examiner* — Joseph Suh
(74) *Attorney, Agent, or Firm* — Dentsply Sirona Inc.

(57) ABSTRACT

The invention relates to a measurement system for optically measuring an object, comprising a dental camera and an optical attachment. In this case the optical attachment comprises at least one lens, which is shaped and arranged in such a way that the optical attachment has a negative focal length so that a measurement field or a measurement volume of the dental camera is enlarged by the optical attachment.

11 Claims, 2 Drawing Sheets

(56) References Cited

U.S. PATENT DOCUMENTS

| | | | | |
|---|---|---|---|---|
| 5,227,607 | A * | 7/1993 | Ishiyama | G03F 7/70091 |
| | | | | 219/121.68 |
| 6,252,717 | B1 * | 6/2001 | Grosskopf | G01B 9/04 |
| | | | | 250/234 |
| 2002/0102520 | A1 * | 8/2002 | Iiyama | A61C 5/77 |
| | | | | 433/215 |
| 2007/0018124 | A1 * | 1/2007 | Nishi | G02B 27/0025 |
| | | | | 250/559.36 |
| 2007/0262960 | A1 * | 11/2007 | Kim | G06K 7/10881 |
| | | | | 345/166 |
| 2008/0017787 | A1 | 1/2008 | Okawa | |
| 2009/0073383 | A1 * | 3/2009 | Coutinho | A61B 3/13 |
| | | | | 351/214 |
| 2009/0298191 | A1 * | 12/2009 | Whitesides | B01L 3/502715 |
| | | | | 436/164 |
| 2010/0189341 | A1 * | 7/2010 | Oota | A61B 5/0037 |
| | | | | 382/154 |
| 2012/0075425 | A1 * | 3/2012 | Thiel | A61B 5/1077 |
| | | | | 348/46 |
| 2013/0038950 | A1 * | 2/2013 | Enomoto | G02B 13/06 |
| | | | | 359/793 |
| 2013/0121525 | A1 * | 5/2013 | Chen | G06T 3/0062 |
| | | | | 382/100 |
| 2013/0162759 | A1 * | 6/2013 | Alakarhu | H04N 5/2625 |
| | | | | 348/36 |
| 2013/0308104 | A1 * | 11/2013 | Nishimori | G03B 21/2066 |
| | | | | 353/37 |
| 2014/0063005 | A1 | 3/2014 | Ahn | |
| 2014/0107471 | A1 * | 4/2014 | Haider | A61B 17/1703 |
| | | | | 600/424 |
| 2014/0146142 | A1 | 5/2014 | Duret | |
| 2014/0198299 | A1 * | 7/2014 | Cheng | A61B 3/0091 |
| | | | | 351/206 |
| 2014/0226003 | A1 * | 8/2014 | Phaneuf | H01J 37/304 |
| | | | | 348/80 |
| 2015/0029309 | A1 * | 1/2015 | Michaeli | A61B 5/0088 |
| | | | | 348/46 |
| 2015/0245771 | A1 * | 9/2015 | Wang | A61B 5/0042 |
| | | | | 600/411 |
| 2016/0008109 | A1 * | 1/2016 | Hauth | A61C 13/34 |
| | | | | 703/1 |
| 2016/0051345 | A1 * | 2/2016 | Levin | A61B 1/24 |
| | | | | 433/29 |
| 2016/0078600 | A1 * | 3/2016 | Perez Pellitero | G06T 7/60 |
| | | | | 382/155 |
| 2016/0183776 | A1 * | 6/2016 | Yamanaka | A61B 1/018 |
| | | | | 433/29 |
| 2017/0189116 | A1 * | 7/2017 | Wu | A61B 18/20 |

FOREIGN PATENT DOCUMENTS

| | | |
|---|---|---|
| JP | 3099615 A | 4/1991 |
| JP | H1156774 A | 3/1999 |

* cited by examiner

METHOD AND MEASUREMENT SYSTEM FOR OPTICALLY MEASURING AN OBJECT

CROSS-REFERENCE TO RELATED APPLICATIONS

This is a continuation application of U.S. Non-Provisional application Ser. No. 15/564,436 filed Oct. 5, 2017, which is a national phase application of International Application No. PCT/EP2016/057870 filed Apr. 11, 2016, which claims the benefit of and priority to German Application No. 102015206341.0 filed Apr. 9, 2015, which are herein incorporated by reference for all purposes

TECHNICAL FIELD

The invention relates to a method and a measurement system for optically measuring an object, comprising a dental camera and an optical attachment.

BACKGROUND OF THE INVENTION

A number of methods and measurement devices for optically measuring a dental object are known from the prior art.

DE 102013223894 B3 discloses a measurement system for optically measuring a dental object, comprising a dental camera, which has a light source, an imaging unit and optical components for projecting a point pattern onto the object to be examined and for transmitting the reflected light beams onto the imaging unit.

EP 0438353 A1 discloses an ugly instrument comprising an intra-oral camera and a laser, wherein a photo lens is arranged upstream of the imaging unit for imaging the entire mouth.

The published document DE 100 43 749 A1 discloses a dental handpiece for image acquisition and means for directing an excitation radiation to a region of the tooth tissue that is to be examined, where in this case the camera is designed in two parts consisting of a sensor head and a camera module. By using different lens tubes having different optical properties, the camera can be equipped with different imaging properties and, as a result, can be adapted to the respective application. In order to transmit the image inside the attachment, a deflection device in the form of a prism is used.

A drawback with this dental camera is that the dental camera can be used only to measure the teeth.

Therefore, the object of the present invention is to provide a measurement system that is used for optically measuring and that can generate an image of not only the teeth, but also larger objects.

SUMMARY OF THE INVENTION

The invention relates to a measurement system for optically measuring an object, comprising a dental camera and an optical attachment. In this case the optical attachment comprises at least one lens, which is shaped and arranged in such a way that the optical attachment has a negative focal length, so that a measurement field or a measurement volume of the dental camera is enlarged by the optical attachment.

The dental camera may be any hand-held dental camera, which is based on a two-dimensional or even on a three-dimensional measurement method.

The object may be the patient's teeth or the patient's face. The optical attachment may be provided with fastening means in order to be fastened to a conventional dental camera. The fastening means may correspond, for example, to the fastening means of an already known mirror sleeve.

The fastening means may comprise, for example, a snap-lock mechanism and a leaf spring, so that when the attachment is mounted on the dental camera, it snaps in and, in so doing, is fixed in its position relative to the dental camera.

Therefore, the optical attachment may comprise a single lens or even a lens system consisting of a plurality of optical lenses, which are arranged with respect to each other in such a way and are shaped in such a way that the optical attachment has a negative focal length and expands the measuring volume. The optical attachment may consist, for example, of a plano-convex lens and a convex-planar lens or a concave-convex lens and a convex-concave lens. The measurement field is the area within which the dental camera measures the object. In the case of a three-dimensional optical dental camera, a measurement volume of the object is measured. In the case of a two-dimensional camera this measurement field or in the case of a three-dimensional camera a measurement volume is significantly enlarged by means of the optical attachment, so that larger objects can be measured.

One advantage of the measurement system is that a conventional dental camera can be used not only for measuring the teeth, but also for measuring larger objects, such as the patient's face or a portion of the face, by means of the optical attachment.

Advantageously, the dental camera can be based on a two-dimensional measurement method or a three-dimensional measurement method.

As a result, the optical attachment can be used for both two-dimensional dental cameras and three-dimensional dental cameras.

Advantageously, the dental camera can be based on a two-dimensional video imaging method, a three-dimensional triangulation measurement method, a three-dimensional confocal measurement method or a white light interferometric measurement method.

The three-dimensional triangulation measurement method may be, for example, the well-known fringe projection method, in which a pattern of light and dark fringe is projected onto the object to be measured. Then the projected fringe pattern is taken at a known viewing angle to the projection by means of the dental camera. Using a so-called phase shift method, a projection coordinate that reflects the position of the fringe in the pattern, is determined. At a known triangulation angle between an illuminating beam and an observation beam, the 3D spatial coordinate of the respective measurement point of the object can be determined. In this way, the spatial coordinate is determined for each measurement point of the object, and a three-dimensional image of the surface of the object is calculated.

In the case of the three-dimensional confocal measurement method, the surface of the dental object is gradually sampled, and the focal plane is gradually shifted. The light outside the focal plane is blocked as much as possible by means of a pinhole. The measured image data of the individual steps of different focal planes can be used to calculate a three-dimensional image of the object to be measured.

The two-dimensional video imaging method is a known measurement method, in which a succession of two-dimensional images of the object is generated.

In the case of white light interferometry, a light of low coherence length is used, so that the result is color interferences, when the path length in the reference beam or the object beam is nearly equal. When the path length is changed, the interference pattern is changed, so that the distance from the surface of the object can be determined on the basis of the interference pattern.

The dental camera can also be based on a measurement method that is a combination of a two-dimensional video imaging method and a three-dimensional triangulation method. In this case the three-dimensional image from the triangulation measurement method is superimposed with the color two-dimensional video image, so that a three-dimensional color image is generated. Advantageously, the optical attachment can be detachably connected to the dental camera by means of connecting means.

This aspect allows the user to measure smaller objects, such as teeth, by means of the camera without the attachment and larger objects, such as portions of the face, by means of the camera with the attachment. The fastening means of the optical attachment on the camera are designed in such a way that the optical attachment is arranged in a predefined position and orientation relative to the camera. The connecting means may be, for example, a threaded joint.

Advantageously, the measurement field or the measurement volume of the dental camera can be enlarged by a magnification factor, which is no less than 5, by means of the optical attachment.

Therefore, a typical measurement volume of a dental camera in the form of a cube with an edge length between 15 mm and 20 mm can be expanded to an enlarged measurement volume, which has, for example, an edge length of no less than 30 mm. That volume may also have a much larger edge length, such as, for example, of no less than 100 mm. The edge length of the measurement volume should be chosen in such a way that the relevant parts of the face, such as the mouth, nose and/or eyes, can be registered.

Advantageously, the optical attachment can also comprise a beam deflector, which deflects an illuminating beam and an observation beam of the dental camera to the object.

The beam deflector may be, for example, a mirror or a prism; and in this way the direction of measurement of the image can extend perpendicular to the longitudinal direction of the camera. This feature is advantageous, in particular, when measuring the teeth.

Advantageously, the optical attachment may comprise a plurality of lenses that are shaped in such a way and are arranged with respect to each other in such a way that the optical attachment has a negative focal length.

Thus, as a result, a plurality of optical lenses is used to produce the negative focal length.

Advantageously, the measurement volume of the three-dimensional dental camera in the form of a cube with an edge length between 10 mm and 20 mm can be enlarged to an enlarged measurement volume with an edge length of no less than 30 mm by means of optical attachment.

As a result, a portion of the face can be measured by means of the camera with the attachment.

Furthermore, the invention relates to a method for measuring an object by means of a dental camera with a detachable optical attachment. In this case the optical attachment has a negative focal length, so that a measurement field or a measurement volume of the dental camera is enlarged by means of the optical attachment.

Therefore, the present method makes it possible to measure a larger measurement field by means of a conventional dental camera with the novel optical attachment.

Advantageously, the dental camera may be based on a two-dimensional measurement method or on a three-dimensional measurement method.

This aspect allows the present invention to be also applied to a two-dimensional or three-dimensional dental camera.

Advantageously, the dental camera may be based on a two-dimensional video imaging method, a three-dimensional triangulation measurement method, a three-dimensional confocal measurement method or a white light interferometric measurement method.

As a result, the method can be used for a dental camera that is based on the aforementioned measurement method.

Advantageously, the measurement field or the measurement volume of the dental camera can be enlarged by a magnification factor, which is no less than 5, by means of the optical attachment.

As a result, the measurement field is significantly enlarged.

Advantageously, in a first step, the patient's teeth can be measured by means of the dental camera without the optical attachment, and a first image of the teeth is generated. Then in a second step at least a part of the patient's face is measured by means of the dental camera with the optical attachment with the enlarged measurement field or measurement volume, and a second image of the face is generated. Then the first image of the teeth and the second image of the face are registered to form a composite image.

In this way, the dental camera without attachment can be used to measure the situation of the teeth, and the camera with the attachment can be used to measure at least a portion of the face. In this context, the measured portion of the face may include, for example, the characteristic areas, such as the nostrils, the shape of the chin, and at the same time also the teeth, in particular, the cusp tips of the cuspid teeth.

The imaged teeth can be replaced by the more precise image of the teeth created by means of the camera without attachment during the registration. Such an image, which includes both a part of the face and the teeth, allows the dental technician or the dentist to work out a treatment strategy that takes into account the shape of the face, the width of the nostrils or the shape of the chin. Therefore, this information can be used to design a dental prosthesis. For example, the dental prosthesis can be designed in such a way that the distance between the cusp tips of the two cuspid teeth matches the width of the nostrils, in order to simulate an aesthetic visual impression of natural teeth.

BRIEF DESCRIPTION OF THE DRAWINGS

The invention is explained with reference to the drawings. In the drawings

DETAILED DESCRIPTION OF THE INVENTION

Figure 1:
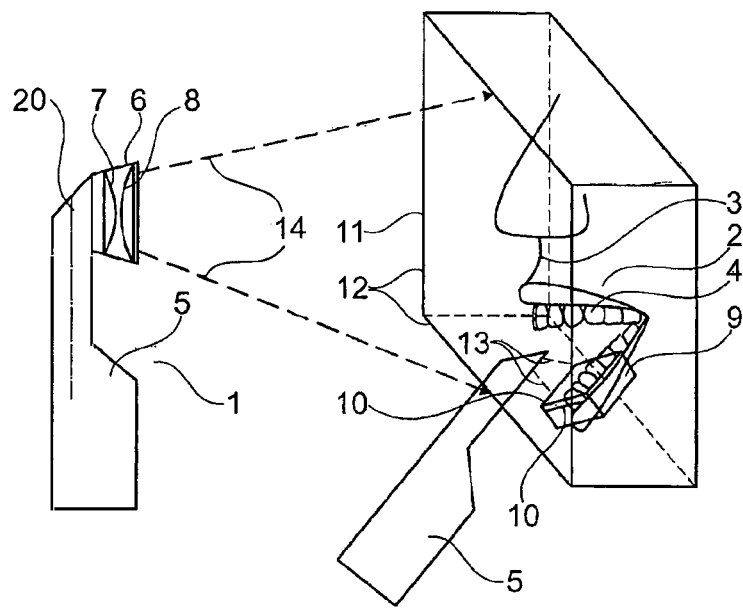
FIG. 1 shows a measurement system comprising a dental camera and an optical attachment.

FIG. 1 shows a measurement system 1 for optically measuring an object 2, which may be the face of the patient 3 and/or the teeth 4 of a patient. The measurement system 1 comprises a conventional dental camera 5 and an optical attachment 6, which has a first plano-convex lens 7 and a second convex-planar lens 8. The two lenses 7 and 8 are shaped in such a way and are arranged relative to the camera 5 in such a way that the optical attachment 6 has a negative focal length. Small objects, such as the teeth 4, are measured by means of the camera 5 without the optical attachment 6, where in this case a measurement volume 9 of the dental camera 5 is relatively small and may have, when shaped like a cube, for example, an edge length 10 between 10 mm and 20 mm. This measurement volume 9 is enlarged to an enlarged measurement volume 11 having an edge length 12 of no less than 100 mm by means of the optical attachment 6. The first illuminating beams 13 of the dental camera 5 without the optical attachment 6 are indicated by the dashed lines. The second illuminating beams 14 of the dental camera 5 with the optical attachment 6 define the limits of the enlarged measurement volume 11.

Therefore, the measurement system 1 can be used for a method in which in the first step the teeth 4 are measured by means of the camera 5 without the optical attachment 6, and then in the second step a portion of the face 3 of the patient is measured by means of the same camera 5 with the optical attachment 6. Then the two images can be subsequently registered with respect to each other. The dental camera 5 may be based on a three-dimensional triangulation method or on a confocal measurement method.

Figure 2:
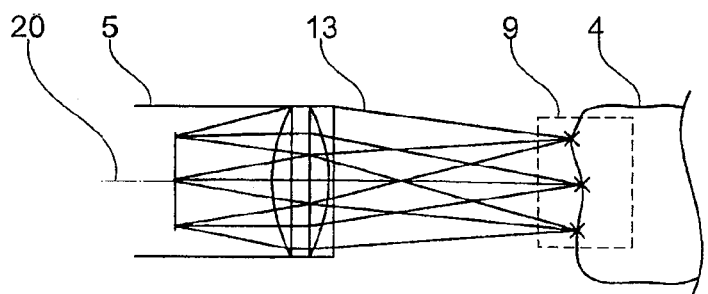
FIG. 2 shows a sketch to illustrate the beam paths of the observation beams of the dental camera without the optical attachment.

FIG. 2 shows a sketch to illustrate the beam length of the illuminating beams 14 of the dental camera 5 without the optical attachment 6. The design of the dental camera 5 may be configured in any way. For example, the dental camera 5 may have a mirror sleeve, which is shown in FIG. 1 and which deflects the illuminating beams 14 perpendicular to the longitudinal axis of the dental camera 5. However, the dental camera 5 may also be used without a mirror sleeve, as shown in FIG. 2. In this case the illuminating beams 14 are emitted in the direction of a longitudinal axis 20 of the dental camera 5. In FIG. 2, a small measurement volume 9 is shown by the dashed line, and this measurement volume measures only a portion of a tooth.

Figure 3:
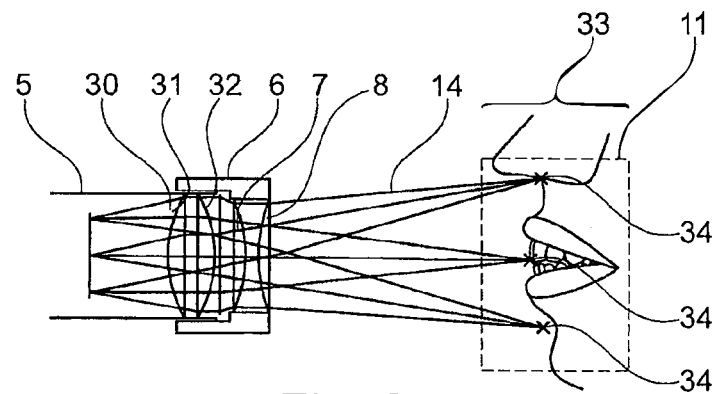
FIG. 3 shows a sketch to illustrate the beam paths of the observation beams of the dental camera with the optical attachment.

FIG. 3 shows a sketch of the camera 5 from FIG. 2 with the optical attachment 6 comprising a first lens 7 and a second lens 8. Therefore, the optical attachment 6 is arranged in the beam path of the illuminating beams 14 of the expanded measurement field 11, in addition to the objective 30 of the dental camera 5, said objective consisting of a first lens 31 and a second lens 32. Therefore, this arrangement allows the measurement volume 9 of the dental camera 5 to be enlarged as far as up to the expanded measurement volume 11, where in this case not only the edge length 10, but also a depth measurement range 33 is enlarged. In the triangulation measurement method, the magnification of the depth measurement range is based on the fact that due to the longer focus the triangulation angle is reduced accordingly. In the confocal measurement method, the longer focus also leads to an enlargement of the depth measurement range. FIG. 3 shows in schematic form the way in which the illuminating beams 14 are widened, and, as a result, the focus points 34 are also farther apart from each other than in FIG. 1.

Figure 4:
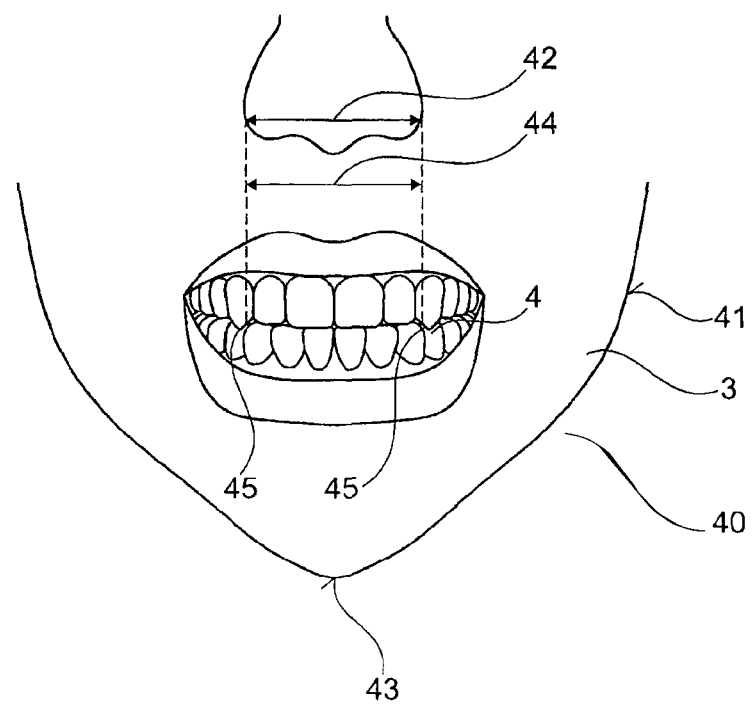
FIG. 4 shows an image of a portion of the face and the teeth by means of the camera with the optical attachment.

FIG. 4 shows an image 40 of a portion of the face 3 and the teeth 4 taken by means of the camera 5 with the optical attachment 6 from FIG. 1. In order to improve the accuracy, the more precise image of the teeth taken by means of the camera 5 without attachment 6 can be registered with the image of the face 3. Because the image of the teeth 4 taken by means of the camera 5 without attachment 6 has a higher resolution. The image 40 of the face 3 enables the dental technician or the dentist to work out a treatment strategy that takes into account the shape of the face 41, the width of the nostrils 42, the shape of the chin 43 and/or the distance 44 from the cusp tips 45 of the cuspid teeth. In the case shown in FIG. 4, the width of the nostrils 42 coincides with the distance 44. This corresponds to a natural condition in most people. Therefore, when designing dental prostheses, the width of the nostrils 42 is also considered in order to simulate natural teeth.

REFERENCE NUMERALS 1 measurement system
2 object
3 patient/patient's face
4 teeth
5 dental camera
6 optical attachment
7 first lens
8 second lens
9 measurement volume
10 edge length
11 enlarged measurement volume
12 edge length
13 first illuminating beams
14 second observation beams
20 longitudinal axis
30 objective
31 first lens
32 second lens
33 depth measurement range
34 focus points
40 image
41 shape of the face
42 width of the nostrils
43 chin
44 distance
45 cusp tips

The invention claimed is:

1. A measurement system for optically measuring an object, comprising:

a dental camera; and an optical attachment, the optical attachment being detachably coupled to the dental camera, and arranged in a beam path with the optical attachment including a plurality of lenses, which are shaped in such a way and are arranged with respect to each other in such a way that the optical attachment has a negative focal length, so that a measurement field or a measurement volume of the dental camera is enlarged by the optical attachment; and wherein the teeth of a patient are measured using the dental camera, and a first image of the teeth is generated, wherein at least one portion of the teeth of the patient is measured using the dental camera with the optical attachment with the enlarged measurement field or enlarged measurement volume; and a second image of the teeth is generated, wherein subsequently the first-image of the teeth and the second image of the teeth are registered to form a composite image wherein optical attachment comprises (i) a plano-convex lens and a convex-planar lens or (ii) a concave-convex lens and a convex-concave lens, and wherein the measurement volume is enlarged to the enlarged measurement volume to have an edge length of no less than 30 mm.

2. The measurement system as in claim 1, wherein the dental camera is based on a two-dimensional measurement method or on a three-dimensional measurement method.

3. The measurement system as in claim 2, wherein the dental camera is based on a two-dimensional video imaging method, a three-dimensional triangulation measurement method, a three-dimensional confocal measurement method or a white light interferometric measurement method.

4. The measurement system as in claim 1, wherein the measurement field or the measurement volume of the dental camera is enlarged by a magnification factor, which is no less than 5, using the optical attachment.

5. The measurement system as in claim 1, wherein the optical attachment additionally includes a beam deflector, which deflects an illuminating beam and an observation beam of the dental camera to the object.

6. The measurement system as in claim 1, wherein the measurement volume of the three-dimensional dental camera in the form of a cube having an edge length between 10 mm and 20 mm is enlarged to the enlarged measurement volume having an edge length of no less than 30 mm using the optical attachment.

7. A method for measuring an object using a dental camera with an optical attachment, comprising:
providing the optical attachment, detachably coupled to the dental camera and having a negative focal length, so that a measurement field or a measurement volume of the dental camera is enlarged by the optical attachment,
measuring, at a first time, using the dental camera without the optical attachment attached, a first portion of the teeth of a patient, to generate a first image of the teeth,
measuring, at a second time, using the dental camera with the optical attachment having the enlarged measurement field or enlarged measurement volume, the second time being different from the first time, a second portion of the teeth of the patient; to generate a second image of the teeth,
registering, responsive to measuring the first portion of the teeth and the second portion of the teeth, the first image of the teeth and the second image of the teeth to form a composite image,
wherein the measurement volume is enlarged to the enlarged measurement volume to have an edge length of no less than 30 mm.

8. The method as in claim 7, wherein the dental camera is based on a two-dimensional measurement method or on a three-dimensional measurement method.

9. The method as in claim 8, wherein the dental camera is based on a two-dimensional video imaging method, a three-dimensional triangulation measurement method, a three-dimensional confocal measurement method or a white light interferometric measurement method.

10. The method as in claim 7, wherein using the optical attachment the measurement field or the measurement volume of the dental camera is enlarged by a magnification factor that is no less than 5.

11. The method of claim 7 further comprising; providing the optical attachment as a (i) a plano-convex lens and a convex-planar lens or (ii) a concave-convex lens and a convex-concave lens.

* * * * *